United States Patent
Ono et al.

(10) Patent No.: US 9,390,509 B2
(45) Date of Patent: Jul. 12, 2016

(54) MEDICAL IMAGE PROCESSING DEVICE, MEDICAL IMAGE PROCESSING METHOD, PROGRAM

(71) Applicant: DAI NIPPON PRINTING CO., LTD., Tokyo (JP)

(72) Inventors: Tetsutaro Ono, Tokyo (JP); Tomoaki Goto, Ichikawa (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 8 days.

(21) Appl. No.: 14/347,266

(22) PCT Filed: Sep. 19, 2012

(86) PCT No.: PCT/JP2012/073877
§ 371 (c)(1),
(2) Date: Mar. 26, 2014

(87) PCT Pub. No.: WO2013/047278
PCT Pub. Date: Apr. 4, 2013

(65) Prior Publication Data
US 2014/0341471 A1    Nov. 20, 2014

(30) Foreign Application Priority Data
Sep. 26, 2011 (JP) .................... 2011-208436

(51) Int. Cl.
G06T 7/00 (2006.01)
A61B 5/00 (2006.01)
A61B 5/055 (2006.01)

(52) U.S. Cl.
CPC ............. *G06T 7/0081* (2013.01); *A61B 5/0042* (2013.01); *A61B 5/055* (2013.01); *G06T 7/0014* (2013.01); *G06T 2207/10088* (2013.01); *G06T 2207/30016* (2013.01)

(58) Field of Classification Search
USPC .................. 382/100, 173, 128, 130, 131, 132
See application file for complete search history.

(56) References Cited

U.S. PATENT DOCUMENTS

2008/0069446 A1* 3/2008 Ancelin .................... 382/181
2009/0252391 A1* 10/2009 Matsuda et al. ........... 382/131
2009/0279778 A1   11/2009 Ekin

FOREIGN PATENT DOCUMENTS

JP    A-2005-237441    9/2005
JP    A-2009-541838    11/2009
(Continued)

OTHER PUBLICATIONS

Ashburner et al., "Unified segmentation," *NeuroImage*, 2005, pp. 839-851, vol. 26, Elsevier Inc.
(Continued)

*Primary Examiner* — Utpal Shah
*Assistant Examiner* — Kate R Duffy
(74) *Attorney, Agent, or Firm* — Oliff PLC

(57) ABSTRACT

Provided is a medical image processing device capable of notifying the diagnosis personnel that a segmentation error has occurred or may have occurred during tissue segmentation processing. This medical image processing device specifies a gray matter image of a subject, smoothes the gray matter image, and, in accordance with an elevation function for calculating an absolute Z score, calculates an elevation value. Next, the medical image processing device compares the evaluation value with a pre-defined threshold value and determines the segmentation result, and, if the separation result is determined to be abnormal, warns that segmentation result is abnormal and displays a segmentation result display screen showing the segmentation result.

10 Claims, 8 Drawing Sheets

(56) References Cited

FOREIGN PATENT DOCUMENTS

| WO | WO 2007/023522 A1 | 3/2007 |
|----|----|----|
| WO | WO 2007/148284 A2 | 12/2007 |
| WO | WO 2011/040473 A1 | 4/2011 |

OTHER PUBLICATIONS

International Search Report issued in International Application No. PCT/JP2012/073877 dated Oct. 23, 2012.

English-language translation of International Preliminary Report on Patentability issued in International Application No. PCT/JP2012/073877 dated Apr. 1, 2014.

Feb. 5, 2015 Extended Search Report issued in European Application No. 12837541.7.

Xingchang et al., "Quantitive Analysis of MRI Signal Abnormalities of Brain White Matter Wtih High Reproducibility and Accuracy," Journal of Magnetic Resonance Imaging, 2002, vol. 15, pp. 203-209.

\* cited by examiner

FIG 8

Threshold Value = 0.80

|   | Terms of Segmentation Result | Number of Errors Identified | Number of Normal Identified | Total | Sensitivity | Specificity |
|---|---|---|---|---|---|---|
| 1 | Normal Segmentation Result | 4 | 801 | 805 | — | 99.5% |

|   | Terms of Segmentation Result | Number of Errors Identified | Number of Normal Identified | Total | Sensitivity | Specificity |
|---|---|---|---|---|---|---|
| 2 | Contain too much white matter | 4 | 0 | 4 | 100.0% | — |
| 3 | Contain too much cerebrospinal fluid | 13 | 0 | 13 | 100.0% | — |
| 4 | Almost no gray matter | 0 | 0 | 0 | 0 | — |
| 5 | Large deviation of overall shape and position | 8 | 0 | 8 | 100.0% | — |
| 6 | Too much noise and blur | 4 | 0 | 4 | 100.0% | — |
| 7 | Lacking large area | 0 | 0 | 0 | 0 | — |
|   | Total (2-7) | 29 | 0 | 29 | 100.0% | — |

MEDICAL IMAGE PROCESSING DEVICE, MEDICAL IMAGE PROCESSING METHOD, PROGRAM

TECHNICAL FIELD

The present invention relates to a medical image processing device and the like that performs diagnosis support for each disease by inputting brain image taken by MRI (Magnetic Resonance Imaging) and performing image processing.

BACKGROUND ART

The inventors of the present invention have developed VSRAD (registered trademark) (Voxel-Based Specific Regional Analysis System for Alzheimer's Disease), which is a diagnosis support system for early stage AD (Alzheimer's Disease). VSRAD is an image processing/statistical analysis software for detecting levels of atrophy in the vicinity of the parahippocampal gyrus (=region of interest), which is characteristically seen in early stage, including prodromal stage, Alzheimer-type dementia, from MRI images.

In VSRAD (registered trademark), the level of atrophy in the region of interest is automatically analyzed, and a Z-score map is superimposed on the MRI brain image. Z-score is a value that indicates the amount of displacement from the average value, in terms of standard deviation, when the image of the test subject and the average image of a healthy subject are statistically compared. In a Z-score map, as in thermography, the distribution of the Z-score is displayed in color according to the Z-score value and is superimposed on the brain image of the test-subject. The diagnostician can visually confirm the degree of atrophy by the Z-score map.

In VSRAD (registered trademark), technologies such as VBM (Voxel Based Morphometry) (see Patent Document 1) and DARTEL (Diffeomorphic Anatomical Registration using Exponentiated Lie algebra) (see Patent Document 2) are used.

VBM is a technology of performing image processing on brain image obtained by imaging the head area of the test subject in units of voxel, which is a three-dimensional picture element. DARTEL shows superior accuracy in spatial standardization processing, compared to conventional VBM, and shows promise in improving diagnostic performance by image statistic analysis for Alzheimer's disease. Here, spatial standardization processing refers to performing broad correction for the size of the entire brain, and local correction for the partial size, in order to internalize the anatomical difference of the brain image between individuals.

In a MRI brain image (especially T1-emphasized MRI brain image), three types of tissue are included, which are the gray colored gray matter corresponding to the nerve cells, the brighter colored white matter corresponding to the nerve fiber, and the almost-black cerebrospinal fluid. By using DARTEL, lesions and degrees of atrophy, which are abnormalities, in the white matter extracted by tissue segmentation of the MRI brain image of the test subject, can be accurately evaluated (see Patent Document 2).

PRIOR ART DOCUMENT

Patent Documents

[Patent Document 1] JP-A-2005-237441
[Patent Document 2] WO2011/040473

SUMMARY OF THE INVEVTION

Problem to be Solved by the Invention

Incidentally, in the tissue segmentation process, there are cases where the gray matter tissue and the white matter tissue are not accurately segmented, due to various reasons. (Hereinafter, such cases are referred to as "segmentation error".) When using conventional VBM, by confirming the Z-score map, the occurrence of segmentation error could easily be distinguished. For example, in the Z-score map, when the area in which the degree of atrophy is advanced is colored in red, if a segmentation error occurs, the entire brain, including those regions other than the vicinity of the parahippocampal gyrus, turns red. Thus, it was obvious that the Z-score was calculated as an abnormal value due to a segmentation error, and the occurrence of segmentation error could easily be detected.

In contrast, when using DATEL, because spatial standardization processing is made remarkably powerful compared to conventional VBM, a similar Z-score map is displayed, even when a segmentation error occurs. That is, even when a segmentation error occurs, at times, the entire brain, including those regions other than the vicinity of the parahippocampal gyrus, may not turn red. Thus, when using DATEL, it is difficult to detect the occurrence of segmentation error, even by confirming the Z-score map. In addition, if a diagnosis is made without the diagnostician noticing the segmentation error, it could possibly lead to a critical misdiagnosis. Therefore, a system that notifies the diagnostician of the occurrence or possible occurrence of segmentation error during the tissue segmentation process is desired.

The present invention was made in view of the above-described problems, and its object is to provide a medical image processing device etc., which can notify the diagnostician of the occurrence or possible occurrence of segmentation error in the tissue segmentation process.

Means for Solving the Problems

In order to achieve the aforementioned object, the first invention is a medical image processing device, comprising: an input means for inputting brain image of a test subject; a segmentation means for segmenting gray matter tissue by performing a tissue segmentation process on the brain image of the test subject; a memorizing means for saving an image group of gray matter tissues of healthy subjects; an output means for outputting diagnosis support information based on statistical comparison between the gray matter tissue image of the test subject obtained by the segmentation means and the image group of gray matter tissues of healthy subjects; and a distinguishing means for distinguishing between normal and abnormal result of segmentation by the segmentation means, based on the voxel value of the gray matter tissue for the brain image of the test subject and per-voxel statistical value of the gray matter tissue for the brain image group for which the tissue segmentation process has been performed normally. The first invention allows notification of the occurrence or possible occurrence of segmentation error in the tissue segmentation process to the diagnostician. In particular, since the segmentation result by the tissue segmentation process is automatically distinguished, no burden is placed on the diagnostician.

The distinguishing means in the first invention preferably distinguishes whether or not the segmentation result by the segmentation means is normal by comparing the absolute Z-score of the voxel value of the gray matter tissue for the brain image of the test subject against a predefined threshold value. This enables accurate distinction of the segmentation result by the tissue segmentation process.

Preferably, the first invention further comprises: a memorizing means for memorizing the voxel value or the per-voxel statistical value of the gray matter tissue for the brain image group for which the tissue segmentation process has been performed normally; and a reflection means for reflecting the voxel value of the gray matter tissue for the brain image of the test subject, which was recognized as being normal by the distinguishing means, to the memorizing means. This enhances the accuracy of the calculation process of the evaluation value (absolute Z-score), which eventually leads to a more accurate distinguishing process.

It is preferable that the first invention further comprises: a warning means for outputting warning information when the distinguishing means recognizes the result of the segmentation as an abnormal result. This prevents the diagnostician from making a misdiagnosis by not noticing the segmentation error.

It is preferable that the first invention further comprises: a display means for displaying the segmentation result by the segmentation means when the distinguishing means recognizes the result of the segmentation as an abnormal result. This removes some burden for the diagnostician.

The second invention is a medical image processing method, comprising: an input step of inputting brain image of a test subject; a segmentation step of segmenting gray matter tissue by performing a tissue segmentation process on the brain image of the test subject; an output step of outputting diagnosis support information based on statistical comparison between the gray matter tissue image of the test subject obtained by the segmentation step and the image group of gray matter tissues of healthy subjects; and a distinguishing step of distinguishing between normal and abnormal result of segmentation in the segmentation step, based on the voxel value of the gray matter tissue for the brain image of the test subject and the per-voxel statistical value of the gray matter tissue for the brain image group for which the tissue segmentation process has been performed normally. The second invention allows notification of the occurrence or possible occurrence of segmentation error in the tissue segmentation process to the diagnostician. In particular, since the segmentation result by the tissue segmentation process is automatically distinguished, no burden is placed on the diagnostician.

The third invention is a program for performing: an input means for inputting brain image of a test subject; a segmentation means for segmenting gray matter tissue by performing a tissue segmentation process on the brain image of the test subject; a memorizing means for saving an image group of gray matter tissues of healthy subjects; an output means for outputting diagnosis support information based on statistical comparison between the gray matter tissue image of the test subject obtained by the segmentation means and the image group of gray matter tissues of healthy subjects; and a distinguishing step of distinguishing between normal and abnormal result of segmentation in the segmentation step, based on the voxel value of the gray matter tissue for the brain image of the test subject and the per-voxel statistical value of the gray matter tissue for the brain image group for which the tissue segmentation process has been performed normally, in a computer. By installing the program of the third invention into a general computer, the medical image processing device of the first invention can be obtained, and the medical image processing method of the second invention can be performed.

Advantageous Effect of the Invention

The present invention provides a medical image processing device that can notify a diagnostician of the occurrence or possible occurrence of segmentation error in the tissue segmentation process and the like.

BRIEF DESCRIPTION OF THE DRAWINGS

FIG. 8 is a figure that shows the sensitivity and specificity when the threshold value is 0.8.

DESCRIPTION OF PREFERRED
EMBODIMENTS OF THE INVENTION

Figure 1:
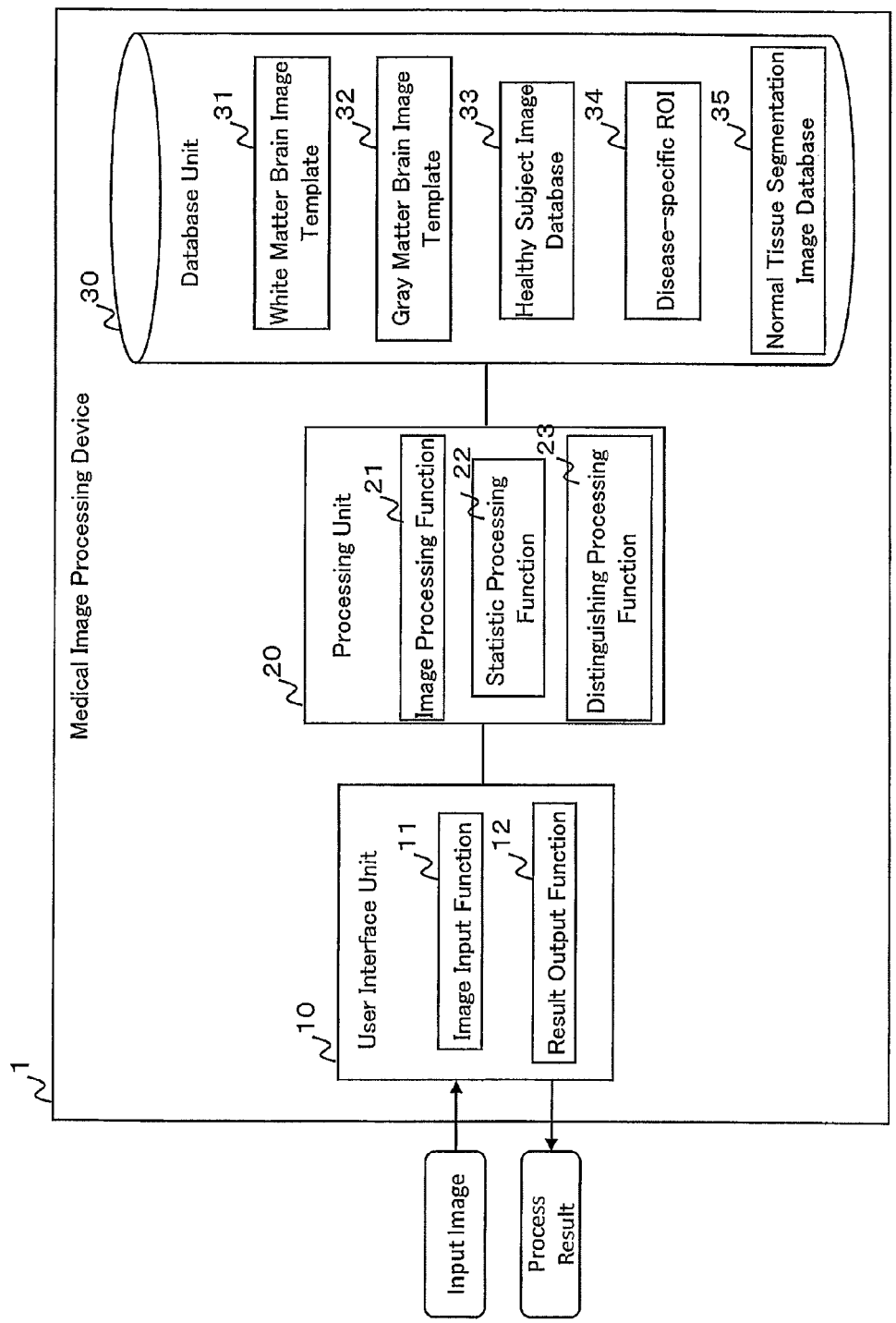
FIG. 1 is a block diagram that shows the outline of the medical image processing device.

Hereinafter, embodiments of the present invention will be described in detail with reference to the accompanying figures. FIG. 1 is a block diagram that shows the outline of the medical image processing device. The medical image processing device 1 is constructed by installing a program for performing the medical image processing method of the embodiment of the present invention into a computer. First, the hardware composition of the computer will be described.

The computer comprises a control unit, a memory unit, an input unit, I/O (Input/Output interface) etc. The control unit is composed of CPU (Central Processing Unit), ROM (Read Only Memory), RAM (Random Access Memory) etc. The CPU performs the program stored in the memory unit, ROM, or recording media, by calling onto the work memory region of the RAM, drive controls various devices, and executes the later-described computer process. The ROM is a non-volatile memory and permanently holds programs such as the computer's boot program and BIOS etc., data and such. The RAM is a non-volatile memory and temporarily holds program and data loaded from the memory unit, ROM, and recording media etc., while being equipped with a work area that is used by the control unit 21 to perform various processes.

The memory unit is, for example, a HDD (Hard Disk Drive), and stores the program that the control unit executes, data that is necessary to execute the program, OS (Operating System), and such. As for the program, a control program that corresponds to the OS, and application program for the computer to execute the later-described processes are stored. Each of these program codes are read accordingly by the control unit, transferred to the RAM, read by the CPU, and executed as various means.

The display unit comprises a display device such as a liquid crystal panel etc. and a logic circuit or such (video adapter etc.) for realizing the video function of the computer by cooperating with the display device. The input unit is for inputting data and comprises input devices such as, for example, a keyboard, a pointing device such as a mouse, and a numerical key pad. Operation instructions, motion instructions, data input and such to the computer can be performed via the input unit. Note that the display unit and the input unit may be integrated as with a touch panel display.

I/O is the port etc., for connecting peripheral equipments (for example, printer, network equipments etc.) to the computer. The computer performs data transfer with the peripheral equipments via the I/O. Further, the computer transfers data with the medical imaging device (such as MRI) and the medical image management server via network equipments etc.

Next, functions of the medical image processing device 1 will be described with reference to FIG. 1. As shown in FIG. 1, the medical image processing device 1 is equipped with a user interface unit 10, a processing unit 20 and a database unit 30.

The user interface unit 10 comprises an image input function 11 for inputting MRI image as an input image and a result output function 12 that displays the result processed by the processing unit 20.

The processing unit 20 comprises an image processing function 21 that processes MRI image inputted by the user interface unit 10, a statistical processing function 22 that performs various statistical operations, and a distinguishing process function 23 that distinguishes whether the result by the image processing function 21 is normal or abnormal.

In the database unit 30, the white matter brain image template 31, the white matter brain image template 32, the healthy subject image database 33, the disease-specific ROI 34, and the normal tissue segmentation image database 35 etc., which are used in the later-described processing unit 20, are stored.

The medical image processing device of the present embodiment supports diagnosis by the diagnostician by performing: (1) the diagnosis support information output process, in which a diagnosis support information is outputted based on the MRI brain image of the test subject; and (2) the image processing result distinguishing process, in which whether the image processing result in the diagnosis support information output process is normal or not is determined, and a warning information is outputted when the image processing result is not normal.

Hereinafter, as an example of the diagnosis support information output process, the first embodiment disclosed in WO 2011/040473 (Patent Document 2) will be described. In the present embodiment, only a flowchart is shown in the figure, and the process flow will be described.

Figure 2:
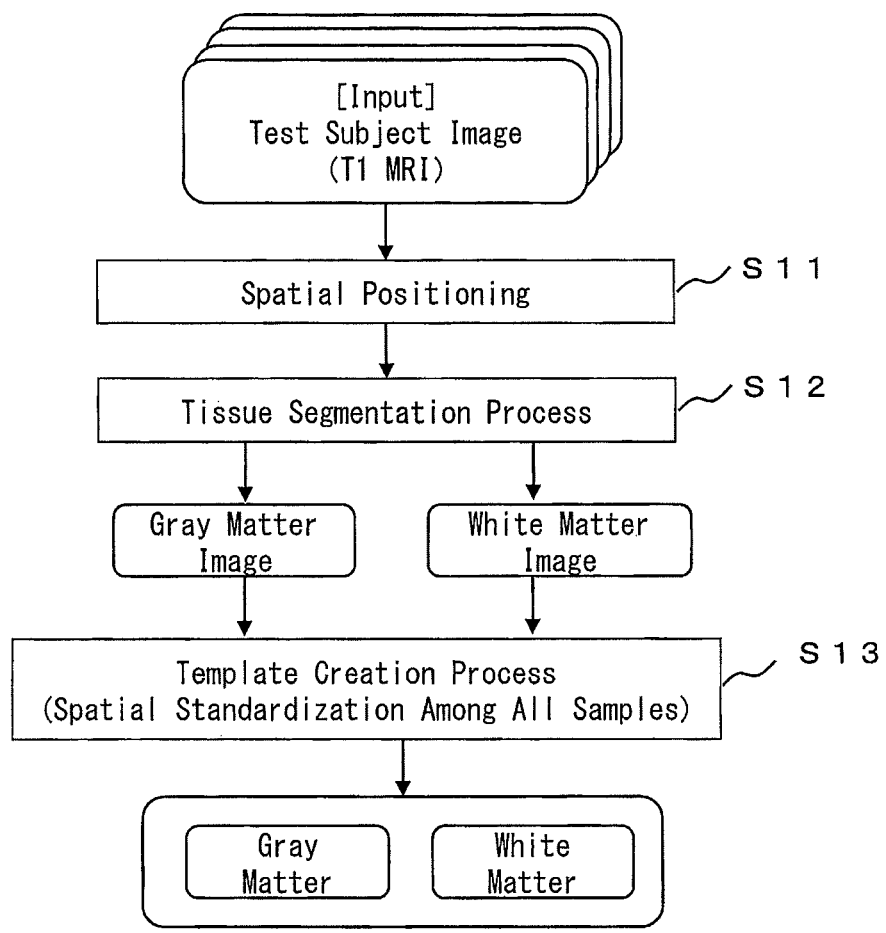
FIG. 2 is a flowchart that shows the preliminary treatment for the medical image processing method.
Figure 3:
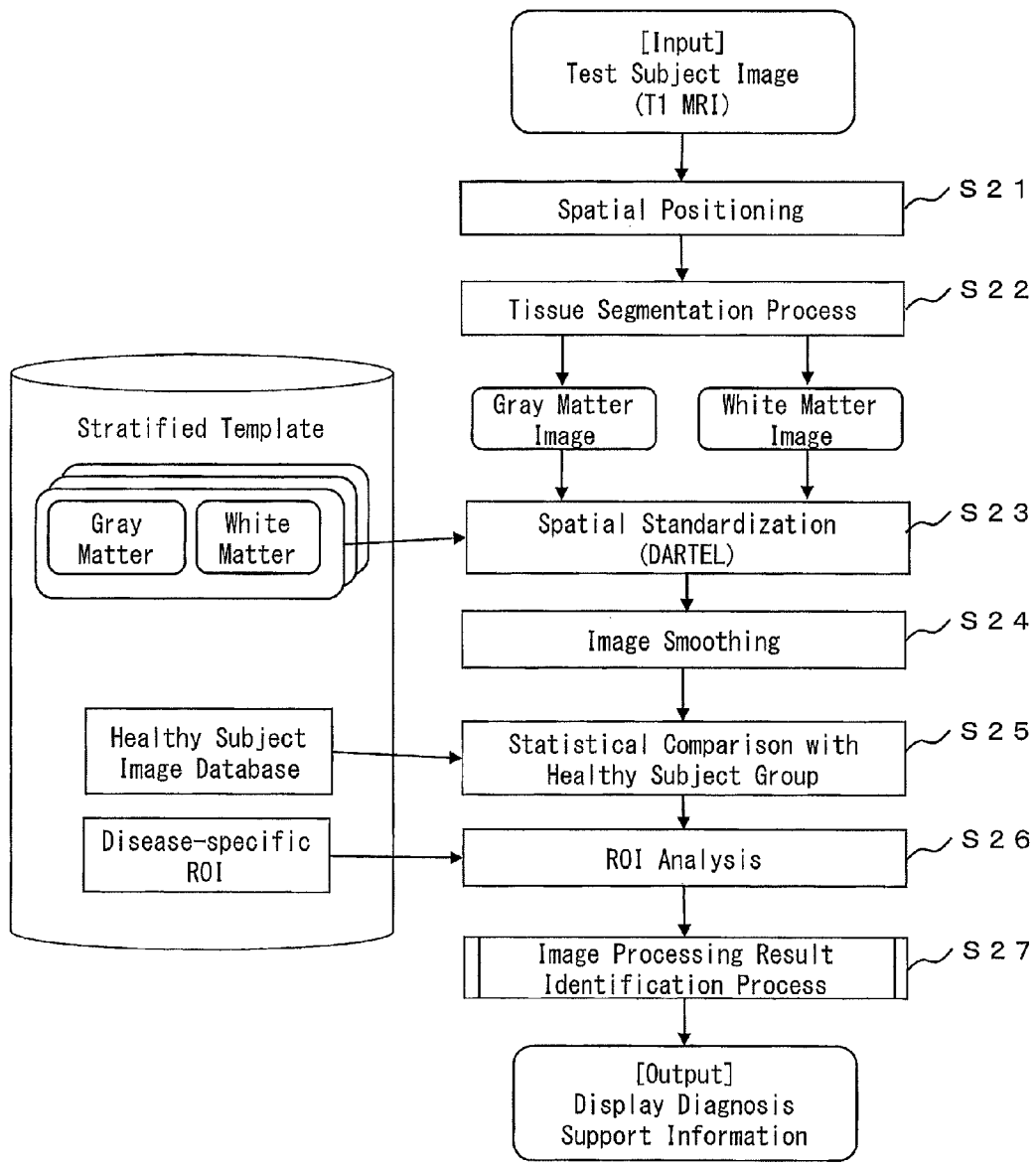
FIG. 3 is a flowchart that shows the diagnosis support information creation process in the medical image processing method.

FIG. 2 is a flowchart that shows the preliminary treatment for the medical image processing method. In the preliminary treatment of FIG. 2, a template that is to be used in the spatial standardization in step 23 of the diagnosis support information creation process of FIG. 3 is created.

As shown in FIG. 2, the medical image processing device 1 input as many T1-emphasized MRI brain images of healthy subjects (test subject image in FIG. 2) as possible.

The MRI brain images obtained from each test subjects are subjected to preliminary treatment. More particularly, for example, 100 to 200 T1-emphasized MRI brain images taken at slices of specified thickness so as to include the entire brain of the test subject are inputted. Further, the slice images are subjected to resampling so that the lengths of each side of the voxel in the slice images are equalized beforehand. Here, voxel is a coordinate unit of the image that includes "thickness", and corresponds to pixel in a two dimensional image.

After inputting the MRI brain image subjected to such preliminary treatment, whether or not the imaging direction and resolution of the slice image is in accordance with conditions pre-set in the system is checked.

As described above, when it is confirmed that the MRI brain image conforms to the setting conditions, the medical image processing device 1 performs a spatial positioning process (step 11).

This corresponds to the correction of spatial position and angle by affine transformation, in order to enhance accuracy when comparing the inputted brain image to a standard brain image.

After such spatial positioning is completed, the medical image processing device 1 performs a tissue segmentation process (step 12), extracts the white matter tissue and the gray matter tissue individually, and creates a white matter image and a gray matter image. Note that although in this embodiment of the present invention, the tissue segmentation process is described as segmenting white matter and gray matter, it is possible to output the diagnosis support information based on statistical comparison between the gray matter tissue image of the test subject obtained by the tissue segmentation process and the gray matter tissue image group of healthy subjects, as long as the gray matter tissue is correctly segmented. Accordingly, it is sufficient for the tissue segmentation process to segment at least the gray matter.

The T1-emphasized MRI brain image includes three types of tissue, which are the white matter presenting high signal value that corresponds to the nerve fiber, the gray matter presenting intermediate signal value that corresponds to the nerve cells, and the cerebrospinal fluid that presents low signal value. Thus, the medical image processing device 1 performs the extraction process of the white matter tissue and the gray matter tissue by focusing on the difference in the signal value. This process is described in JP-A-2005-237441 (Patent Document 1). In the present embodiment, an integrated tissue segmentation process, which shows higher extraction accuracy than the method in Patent Document 1, is performed. The integrated tissue segmentation process is a tissue segmentation method in which standardization, tissue segmentation, and correction of unequal signals are incorporated into one model. Details are described in J. Ashburner and K. J. Friston, Unified segmentation. Neuro Image, 2005; 26: 839-851. The integrated tissue segmentation process is characteristic in that a conversion field, which shows the correlation between the coordinates of the MRI image and the coordinates of the standard brain, is created besides the white matter image and the gray matter image. The conversion field is used in the later-described standardization.

Thus, the medical image processing device 1 obtains a multitude of white matter images and gray matter images that are three dimensionally extracted from the white matter and gray matter by the tissue segmentation of MRI brain images of many healthy subjects, as samples.

Such medical image processing device 1 creates white matter images as samples by performing tissue segmentation on a multitude of MRI brain images of healthy subjects and extracting white matter, and creates a white matter template by performing spatial standardization among all such samples (step 13). Similarly, the medical image processing device 1 creates gray matter images as samples by performing tissue segmentation on a multitude of MRI brain images of healthy subjects and extracting gray matter, and creates a gray matter template by performing spatial standardization among all such samples.

Here, the DARTEL algorithm is applied for the spatial standardization. As described previously, DARTEL shows superior accuracy in spatial standardization processing compared to conventional VBM, and is expected to be a technology that improves diagnostic performance of Alzheimer's disease by image statistical analysis. Further, because the spatial standardization in DARTEL is performed more precisely than conventional methods, white matter can also be the evaluation target, instead of just the gray matter.

In the template creation process of step 13, the medical image processing device 1 creates a stratified template for each of the white matter and gray matter, according to properties such as age and gender of the test subject, and saved as white matter brain image template 31 and gray matter image template 32 in database unit 30.

As mentioned above, the medical image processing device 1 prepares the diagnosis support information shown in FIG. 3, assuming that the white matter and gray matter templates created as such are prepared according to age and gender. Hereinafter, the white matter and gray matter templates are referred to as "DARTEL templates".

FIG. 3 is a flowchart that shows the diagnosis support information creation process in the medical image processing method. As shown in FIG. 3, in the diagnosis support information creation process the T1-emphasized MRI brain image of the test subject to be diagnosed is the input data.

As with the preliminary treatment of FIG. 2, the medical image processing device 1 inputs the test subject image and performs resampling of the slice images so that the lengths of each side of the voxel in the slice images are equalized beforehand. Then the medical image processing device 1 performs a spatial positioning process as in step 11 of the preliminary treatment process (step 21).

After the above spatial positioning process is completed, the medical image processing device 1 performs a tissue segmentation process (step 22). This tissue segmentation process is similar to that of step 12 in the preliminary treatment process. The medical image processing device 1 extracts the white matter and gray matter and creates a white matter image and a gray matter image of the test subject.

As mentioned above, the medical image processing device 1 then performs a spatial standardization process on the thus created white matter image and gray matter image of the test subject (step 23). Here, a DARTEL algorithm is applied for the spatial standardization, as with step 13 of the preliminary treatment process.

This spatial standardization process is performed as a broad correction for the size of the entire brain and a local correction for the partial size, in order to internalize the anatomical difference of the brain image among individuals. Hereinafter, for the sake of convenience, description will be centered on the gray matter but a substantially same process is performed for the white matter, as well.

The spatial standardization process of DARTEL in step 23 is composed of the following three steps of processing:
(Step 23-1) Initial position determination process
(Step 23-2) Conversion process to DARTEL template
(Step 23-3) Conversion process to standard brain template In the initial position determination process of step 23-1, the initial position is determined for the gray matter image and the white matter image using the conversion field to the standard brain obtained by the above-described integrated tissue segmentation process. This process is characteristic in that the shape of the image does not change, since rigid body conversion is performed.

In the conversion process to DARTEL template of step 23-2, the medical image processing device 1 fits the image, for which step 23-1 has been performed, into the shape of the DARTEL template using the DARTEL algorithm.

In the conversion process to DARTEL template of step 23-2, the medical image processing device 1 performs a process of fitting the image fitted to the DARTEL template in step 23-2 into the standard brain template. The conversion field from the DARTEL template to the standard brain template is obtained beforehand, and conversion to the standard brain coordinate system is performed using the conversion field.

In the processes of step 23-2 and step 23-3, the volume can be measured after standardization, because standardization is performed while retaining the sum of the signal value for each voxel, and thus, the volume information is retained.

In step 23-1, linear transformation is performed, in step 23-2 and step 23-3, linear transformation and nonlinear transformation are performed. Using step 23-2 as an example, the medical image processing device 1 performs image processing so that the sum of squares of the error against the average gray matter brain image template 32 created in step 12 read from the database unit 30 becomes minimal, using linear transformation and nonlinear transformation. In this spatial standardization process, first, broad correction for the position, size and angle is made by linear transformation, followed by local correction of shape such as roughness by nonlinear transformation.

The linear transformation performed here is the affine transformation similar to the positioning in step 11. Further, the nonlinear transformation performs transformation on the original image by estimating a distortion place that shows local displacement in the x-direction and y-direction, and using this distortion place.

The process of step 23-2 is a process of fitting the process target image using the DARTEL template created in step 13 as a model. Because the template used is created with high accuracy by applying the DARTEL algorithm, its shape is sharp.

Thus, because each target images for processing are adjusted to become closer in shape with no individual difference by spatial standardization, the accuracy of spatial standardization can be improved and the shape among individuals become similar. However, atrophies and such are reflected on to local density.

The medical image processing device 1 performs image smoothing on the white matter image and gray matter image that has undergone spatial standardization (hereinafter referred to as "standardized brain image" at times) (step 24).

This is a process for improving the S/N ratio of the standardized brain image, as well as for equalizing the smoothness of the image with the image group of healthy subjects, which are later used as standards for comparison, and three dimensional Gaussian kernel is used. The FWHM (full width half maximum) of the filter used for this smoothing is to be about 8 mm.

More specifically, as described in Patent Document 1, the medical image processing device 1 performs three dimensional convolution on the three dimensional brain image and the three dimensional Gaussian function. This corresponds to successively performing one dimensional convolution for each of the x, y, and z directions. By performing smoothing in such manner, individual differences that do not completely match in spatial standardization process can be reduced.

In the process of step 23, the volume information of the brain is saved. Thus, the integrated value of the entirety or the later-described region of interest (ROI) for the process result image of the white matter and gray matter may be measured as the volume before the next concentration value correction is performed, and used as the diagnosis support information.

A concentration value correction of correcting the voxel value for the entire brain is performed on the standardized brain image that has undergone image smoothing, in order to adjust it to the voxel value distribution of the image group of healthy subject, which is later used as the standard for comparison.

Subsequently, the medical image processing device 1 makes a statistical comparison of the result with the healthy subject group (step 25). Here, the MRI brain image of the gray matter (white matter) of the test subject, which has undergone standardization through steps 21 to 24, and the MRI brain image group of the gray matter (white matter) of healthy subjects, which were collected and saved as healthy subject image database 33 in the database unit 30, are comparatively tested. The healthy subject image group used is preferably composed of those in a similar age group as the test subject.

More specifically, the medical image processing device 1 performs a comparative test of 1:N (N is the total number of healthy images) with the healthy image group in voxel units, and detects voxels in which statistically significant difference is seen (presumed to be abnormal).

First, the Z-score, represented by the following equation, is calculated for all voxels.

$$Z = (\mu - x)/\sigma \qquad (1)$$

Here Z: Z-score, $\mu$: average voxel value corresponding to the healthy subject image group, x: voxel value of the test subject image, $\sigma$: standard deviation of the voxel value corresponding to the healthy subject image group.

Thus, the Z-score is a value obtained by taking the difference between the voxel value of the test subject image and the average voxel value of the corresponding voxel value in the healthy subject image group, and scaling by the standard deviation, and indicates the degree of relative decrease in the gray matter (white matter) volume.

Next, an appropriate critical value Z' is determined, and a voxel wherein the Z-score becomes $$Z' < Z \qquad (2)$$

is obtained, and set as a voxel wherein statistically significant difference is observed. Z'=2 is used as the critical value, since abnormality can be presumed at a probability of about 95%. Further, the following equation is also used as a method of assigning a critical value, which includes all areas in which the volume is reduced compared to healthy subjects.

$$0 < Z \qquad (3)$$

Note that the healthy subject database 33 used in step 25 is created by sequentially performing each process of spatial positioning→tissue segmentation process of gray matter (white matter)→spatial standardization→image smoothing etc. of steps 21 to 24, and saved.

Further, in this medical image processing device 1, testing by Z-score is made possible by categorizing the collected healthy subject images according to age groups of, for example, 5 years or 10 years, and saving the average values and standard deviation calculated for each group in the memory unit.

Note that when using the Z-score in such manner, only the average value and standard deviation for each voxel is necessary. Thus, there is an advantage in that after data creation, the image data itself does not have to be saved.

After performing statistical comparison on the standardized brain image of the test subject as described above, the medical image processing device 1 performs a ROI analysis (step 26).

This is a method of setting the region of interest (ROI) of a specified size on the image, when discriminating the presence or absence of abnormalities using the brain image. It is for placing on the brain image, and comparing by setting an ROI of specific size on a specific part that attract attention as being related to a specific disease.

As described in Patent Document 1, this analysis method provides the degree of morbidity by applying the ROI that corresponds to the disease (disease-specific ROI 34) to the voxel and Z-score of the coordinate position in which significant difference from that of healthy subjects were indicated by statistical processing. The two characteristics are as follows.

(Characteristic 1) Prepare ROI (disease specific ROI 34) as a standardized image data corresponding to each disorder of Alzheimer's disease, apply (set) each ROI onto the brain image data of the test subject for the disorder that is conceivable from the symptoms of the test subject, determining the diagnostic result as that with the highest significance based on the Z-score in this ROI.

(Characteristic 2) The disorder is not assessed by the Z-score of the ROI part alone, but a comparison is made between the Z-score map of the entire brain when ROI is not applied, and the Z-score map of the part to which ROI is applied. The purpose of this process is to see the degree of atrophy in the region of interest in relation to the atrophy of the entire brain.

Here, a method of determining whether or not the test subject is affected by disorder A will be described, using as an example a case wherein specific ROIs for disorder A to C are prepared.

The following five parameters are calculated by equation (2) and equation (3) for the Z-score map of the test subject obtained by the statistical comparison of step 25, using ROI corresponding to disorder A.

P1=total Z-score of voxel that satisfy equation (3) in the ROI part/number of voxel that satisfy equation (3) in the ROI part P2=number of voxel that satisfy equation (2) in entire brain/number of voxel in entire brain P3=number of voxel that satisfy equation (2) in ROI part/number of voxel in ROI part

P4=P3/P2

P5=maximum Z-score in all voxels in ROI part

By obtaining properties for a patient group with disorder A beforehand in terms of the five parameters P1 to P5, the test subject can be discriminated as having disorder A when the values of the parameters for the test subject matches them.

Such discrimination result is outputted as diagnosis support information. Further, the values of Z-score and each parameter are outputted as diagnosis support information. Further, as with thermography, a Z-score map, in which the Z-score distribution is indicated in colors according to the Z-score value and superimposed on the brain image of the test subject, is also outputted as diagnosis support information. The diagnosis support information is displayed, for example, in the display unit of the medical image processing device 1.

The medical image processing device 1 of the present embodiment performs an image processing result distinguishing process (step 27) prior to outputting the diagnosis support information. The image processing result distinguishing process will later be described with reference to FIG. 5.

As described above, the medical image processing device 1 performs a diagnosis support information output process. Incidentally, in the tissue segmentation process, segmentation errors, where the gray matter tissue and the white matter tissue are not segmented correctly, occur at times due to various reasons. In the processing result of the medical image processing device 1, which applies DARTEL, in most cases, the occurrence of segmentation error cannot be detected by visual observation of the Z-score map by the diagnostician.

Figure 4:
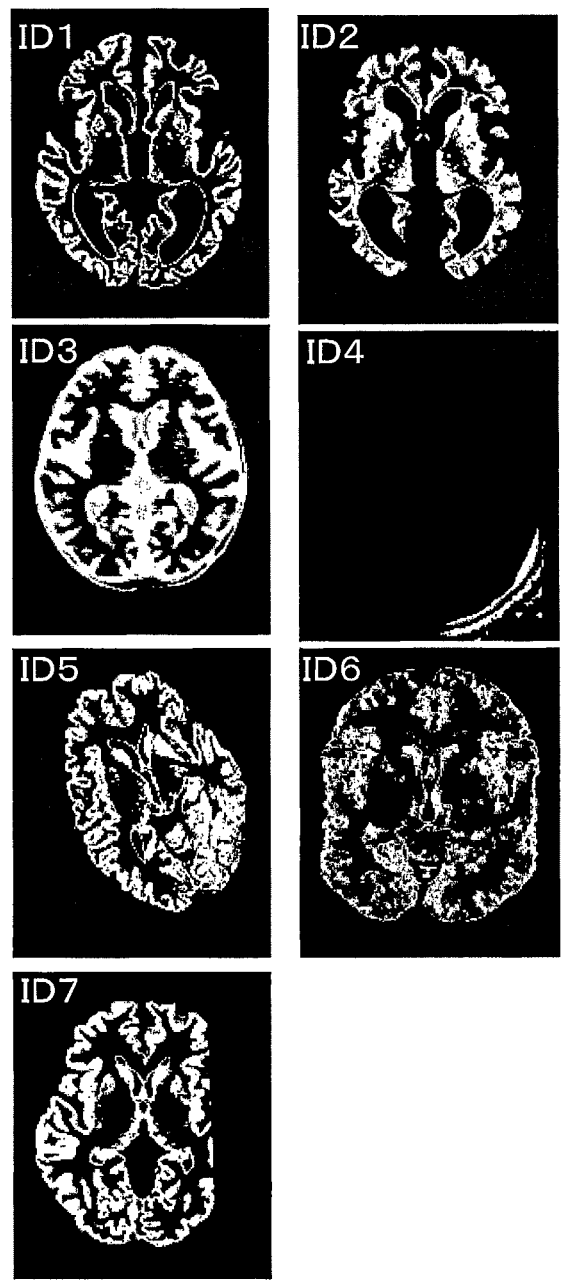
FIG. 4 shows a normal example of the tissue segmentation result and examples of segmentation error.

FIG. 4 shows examples of a normal tissue segmentation result and segmentation errors. ID1 to ID7 are axial (horizontal section) slice images, and the gray matter parts are shown in white, while other parts are shown in black. ID1 is the normal example, ID2 to ID7 are the segmentation error examples. The causes of segmentation error vary, such as movement of the test subject during imaging, deviation in imaging position, and wrong imaging condition.

Images, in which segmentation errors are likely to occur, are as follows:

Image with insufficient contrast between gray matter and white matter.
Image with undesirable SN ratio (signal to noise ratio) (image with noticeable noise).
Image with uneven signal.
Image with artifacts (due to magnetic susceptibility, body motion, folding, etc.)
Image for which the imaging area is too wide.
Image in which tissue degeneration such as white matter infarction is developed in a wide region.

In the image of ID1, segmentation of gray matter and white matter is performed normally, and the gray matter is extracted correctly.

The image of ID2 contains too much white matter. This can be understood when observed by comparing with the image of ID1. In the image of ID2, parts which should be extracted as white matter are extracted as gray matter in the tissue segmentation process.

The image of ID3 contains too much cerebrospinal fluid. This can be understood when observed by comparing with the image of ID1. In the image of ID3, parts which should be extracted as cerebrospinal fluid are extracted as gray matter in the tissue segmentation process.

The image of ID4 shows almost no gray matter. This can be understood when observed by comparing with the image of ID1. In the image of ID4, parts which should be extracted as gray matter are extracted as white matter or cerebrospinal fluid in the tissue segmentation process.

In the image of ID5, deviation of the overall shape and position is large. It appears that the imaging position was not correct for the image of ID5.

In the image of ID6, there is too much noise and blur. This can be understood when observed by comparing with the image of ID1. In the image of ID6, it appears that the imaging conditions were not correct.

The image of ID7 is lacking a large area. This can be understood when observed by comparing with the image of ID1. In the image of ID7, it appears that the imaging area was not correct or that there was a defect in part of the imaging data.

Figure 5:
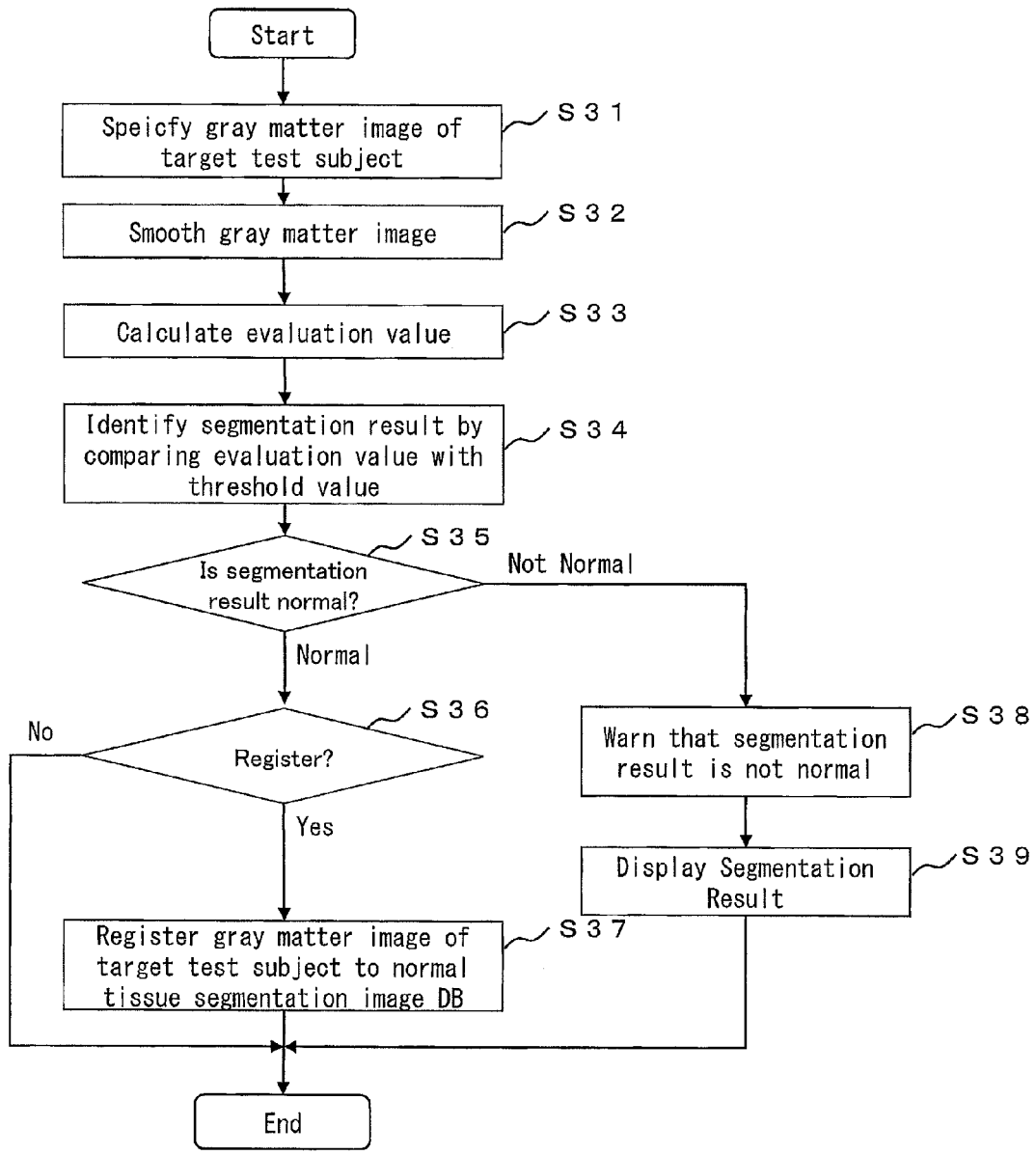
FIG. 5 is a flowchart that shows the tissue segmentation result distinguishing process in the medical image processing method.

In the medical image processing device 1 of the present embodiment, a system that notifies the occurrence or possible occurrence of segmentation error in segmentation results such as those shown in FIG. 4, through the image processing result distinguishing process of FIG. 5, is provided.

FIG. 5 is a flowchart that shows the image processing result distinguishing process of the medical image processing method. The image processing result distinguishing process is performed prior to outputting the diagnosis support information (refer to step 27 in FIG. 3).

As shown in FIG. 5, the medical image processing device 1 selects the gray matter image of the test subject, which was the target for the diagnosis support information creation process (hereinafter referred to as "target test subject" at times) (step 31).

The gray matter image specified in step 31 is, for example, an axial (horizontal section) slice image passing through the origin of the MNI (Montreal Neurological Institute) coordinate system. This image intersects the vicinity of the parahippocampal gyrus (the region of interest in the present embodiment). However, the gray matter image that is to be specified in step 31 is not limited to this example, and may be other slice images. Further, the number of gray matter image specified in step 31 is not limited to one, but may be multiple images.

Next, the medical image processing device 1 performs smoothing of the gray matter image, specified in step 31, of the target test subject (step 32). The smoothing here is similar to the image smoothing process of step 24 in FIG. 3.

The smoothing in step 32 uses, for example, three-dimensional Gaussian kernel. The FWHM (full width half maximum) of the filter used for this smoothing is about 8 mm.

The smoothing in step 32 is a process for removing microstructures in the gray matter to a certain degree and for equalizing the smoothness of the image with the image group registered in the normal tissue segmentation image database 35. In the normal tissue segmentation image database 35, gray matter images, for which the tissue segmentation process of step 22 in FIG. 3 was performed normally (hereinafter referred to as "normal tissue segmentation image" at times), are registered. The medical image processing device 1 performs smoothing, similar to that performed on the gray matter image of the target test subject, on the normal tissue segmentation image, and registers it to the normal tissue segmentation image database 35.

Next, the medical image processing device 1 calculates the evaluation value (step 33) for the image that has been smoothed in step 32, according to a predefined evaluation function. Examples of the evaluation functions are as follows.

[Equation 1]

$$\frac{\sum_{x}^{X}\sum_{y}^{Y}\sqrt{\frac{(input(x,y)-mean(x,y))^2}{SD(x,y)}}}{XY} \quad (4)$$

[Equation 2]

$$\frac{\sum_{x}^{X}\sum_{y}^{Y}\sum_{z}^{Z}\sqrt{\frac{(input(x,y,z)-mean(x,y,z))^2}{SD(x,y,z)}}}{XYZ} \quad (5)$$

[Equation 3]

$$\frac{\sum_{x}^{X}\sum_{y}^{Y}\sqrt{\frac{(input(x,y)-mean(x,y))^2}{SD(x,y)}}}{XY} \quad (6)$$

[Equation 4]

$$\frac{\sum_{x}^{X}\sum_{y}^{Y}\sum_{z}^{Z}\sqrt{\frac{(input(x,y,z)-mean(x,y,z))^2}{SD(x,y,z)}}}{XYZ} \quad (7)$$

[Equation 5]

$$\frac{\sum_{x}^{X}\sum_{y}^{Y}\frac{|input(x,y)-mean(x,y)|}{SD(x,y)}}{XY} \quad (8)$$

-continued

[Equation 6]

$$\frac{\sum_{x}^{X}\sum_{y}^{Y}\sum_{z}^{Z}\frac{|input(x,y,z)-mean(x,y,z)|}{SD(x,y,z)}}{XYZ} \quad (9)$$

Note that the x-axis and y-axis are axes that compose the axial (cross-section). The z-axis is the body axis of the test subject, which cross at a right angle with the axial (cross-section).

Input (x, y) are the voxel values of voxel (x, y) in the gray matter image of the target test subject with the z-axis fixed. Input (x, y, z) is the voxel value of the gray matter image of the target test subject.

Mean (x, y) is the average value per voxel (x, y) for the image group registered in the normal tissue segmentation image database 35, with the position of the z-axis fixed. Mean (x, y, z) is the average value per voxel (x, y, z) of the image group registered in the normal tissue segmentation image database 35.

SD (x, y) is the standard deviation per voxel (x, y) for the image group registered in the normal tissue segmentation image database 35, with the position of the z-axis fixed. Mean (x, y, z) is the standard deviation per voxel (x, y, z) of the image group registered in the normal tissue segmentation image database 35.

X is the number of voxel in the x-axis direction. Y is the number of voxel in the y-axis direction. Z is the number of voxel in the z-axis direction.

The evaluation functions shown in equation (4) to equation (9) are all based on the Z-score indicated in equation (1), and the range is more than or equal to 0. The evaluation value calculated from the evaluation functions of equation (4) to equation (9) and the evaluation function of equation (4) to equation (9) wherein the denominator=1 is generally named as the "absolute Z-score". Note that the evaluation value is not limited to the absolute Z-score, and may be, for example, various modifications based on the aforementioned P1 to P5.

When using the evaluation functions of equations (4), (6) and (8), the medical image processing device 1 specifies one slice of the gray matter image of the target test subject in step 31. On the other hand, when using the evaluation functions of equations (5), (7) and (9), the medical image processing device 1 specifies multiple numbers of the gray matter image of the target test subject that match the Z value (number of voxels in the z-axis direction). Note that even when only one gray matter image of the target test subject is used, as later-described with reference to FIG. 6 to FIG. 8, the segmentation result can be distinguished with high precision.

Thus, in the present embodiment, the normal tissue segmentation image database itself is not used. Hence, in the normal tissue segmentation image database 35, per-voxel statistical values (such as mean (x, y), mean (x, y, z), SD (x, y), and SD (x, y, z) etc.) for the normal tissue segmentation image group may be memorized along with the voxel values of each normal tissue segmentation image. For the later, since the normal tissue segmentation image itself is not memorized, medical information of each test subject can be protected with certainty.

Next, the medical image processing device 1 compares the evaluation value calculated in step 33 against a predefined threshold value, and distinguishes the segmentation result (step 34). The method of defining the threshold value will be described later with reference to FIG. 6 to FIG. 8.

When the medical image processing device 1 determines that the segmentation result is normal ("Normal" in step 35) and the user confirms that the distinguishing result is correct, instruction to register is made via the input unit ("Yes" in step 36), and the voxel value of the gray matter image of the target test subject (for the image smoothed in step 32) is registered in to the normal tissue segmentation image database 35 (step 37). That is, the medical image processing device 1 reflects the voxel value of the gray matter tissue for the brain image of the test subject, which was determined to be normal in step 34, in the normal tissue segmentation image database 35. On the other hand, when the user confirms that this distinguishing result is not correct, and instruction to not register is made via the input unit ("No" in step 36), the medical image processing device 1 ends the process.

Note that when constructing the medical image processing device 1 to memorize per-voxel statistical values of the normal tissue segmentation image group in the normal tissue segmentation image database 35, the following process will be performed in addition to the registration of the voxel value of the gray matter tissue of the target test subject. That is, the medical image processing device 1 reflects the voxel value of the gray matter image of the target test subject onto the memorized per-voxel statistical value of the normal tissue segmentation image group. Then, the medical image processing device 1 registers the statistical value, in which the voxel value of the gray matter image of the target test subject is reflected, in the normal tissue segmentation image database 35.

In either case (the case where the voxel value of the gray matter tissue of the target test subject is registered, or the case where the statistical value, in which the voxel value of the gray matter image of the target test subject is reflected, is registered), the per-voxel statistical value of the normal tissue segmentation image used for the calculation process of the evaluation value will be automatically renewed based on more image groups. Thus, the accuracy of the calculation process of the evaluation value improves, leading to improvement of the accuracy of the distinguishing process.

On the other hand, when the medical image processing device 1 determines that the segmentation result is not normal ("Not Normal" in step 35), it warns that the segmentation result is not normal (step 38). As a means of warning, for example, a message indicating that the segmentation result is not normal may appear on the display unit, or a sound may be outputted. An example of a message indicating the segmentation result to be abnormal is "Check segment results!" and "Probable sgment error!" The screen on which such message is displayed may be the process result display screen or the report output screen for the diagnosis support information.

Next, the medical image processing device 1 displays a segmentation result display screen (step 39). Here, in the segmentation result display screen, in addition to the gray matter image shown in FIG. 4, the image prior to segmentation, the white matter image, and the cerebrospinal fluid image etc. are displayed.

In terms of the entire diagnosis support information creation process, the segmentation result is merely an intermediate result in the creation of the diagnosis support information. Thus, if no problem arises, the diagnostician would rather abbreviate the procedure of confirming segmentation result. Hence, the medical image processing device 1 displays the segmentation result display screen only when the segmentation result is recognized as abnormal.

As described above, the medical image processing device 1 performs an image processing result distinguishing process.

Hereinafter, the method of defining the threshold value in FIG. 5 will be described with reference to FIG. 6 to FIG. 8.

Figure 6:
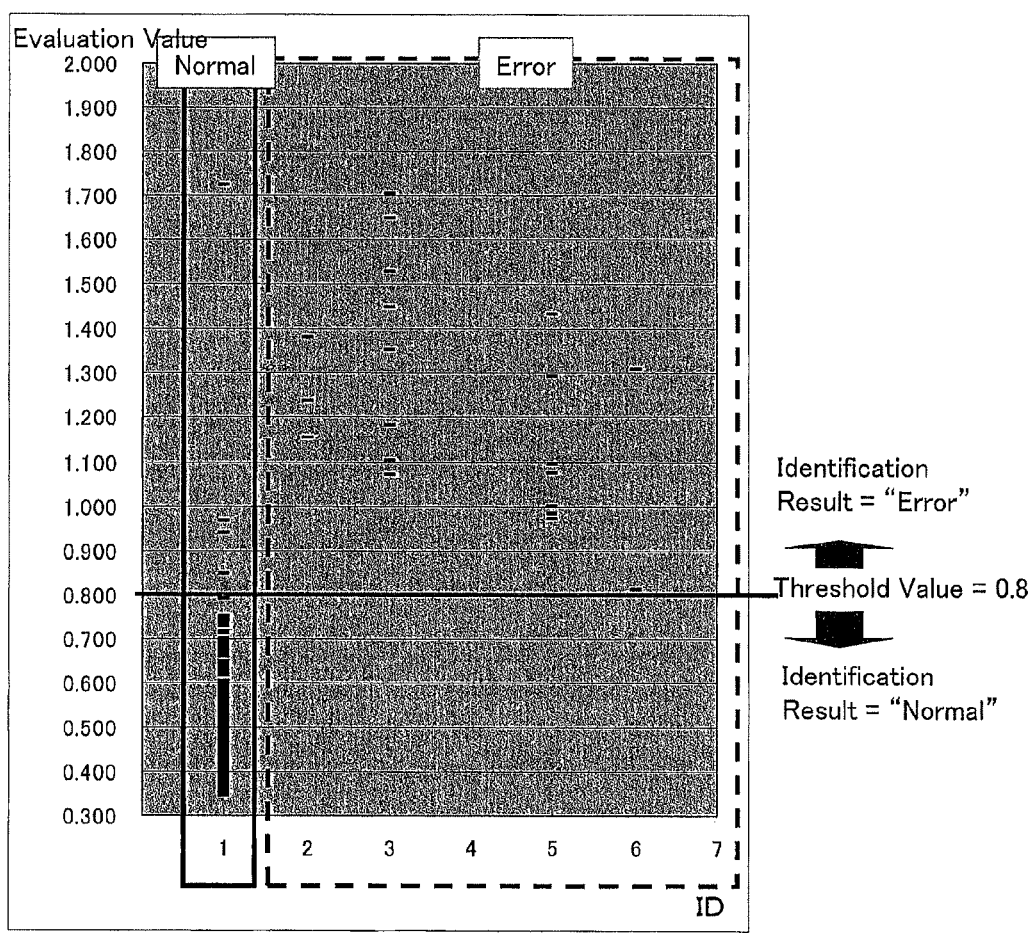
FIG. 6 is a figure that shows the frequency distribution of the evaluation value and the threshold value for each embodiment of the segmentation result.

FIG. 6 is a figure that shows the frequency distribution of the evaluation value according to the terms of the segmentation result and the threshold value. FIG. 7 is a graph that shows the distinguishing performance of the segmentation error. FIG. 8 is a figure that shows the sensitivity and specificity when the threshold value is 0.8.

Figure 7:
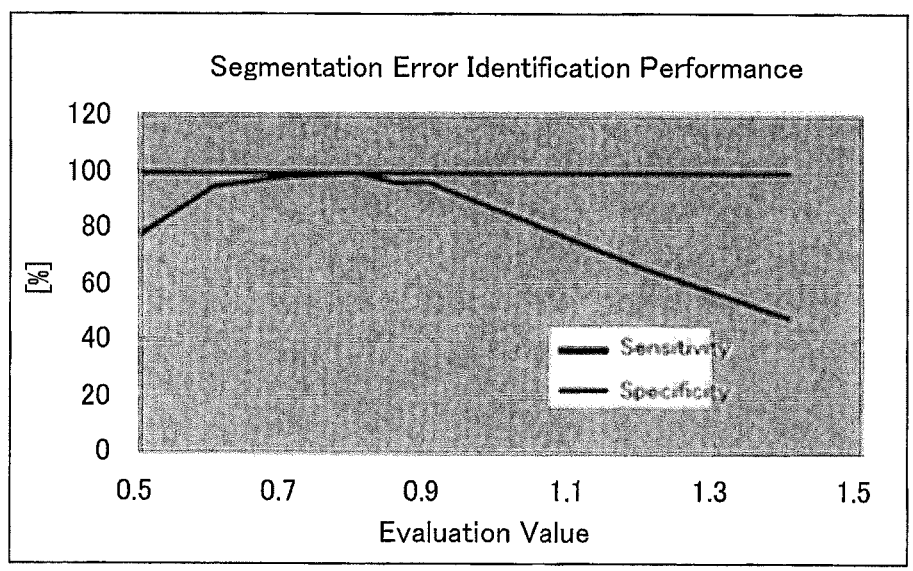
FIG. 7 is a graph that shows the segmentation error distinguishing performance.

FIG. 6 to FIG. 8 are obtained by preparing multiple numbers of segmentation results in accordance to the normal example and error examples of FIG. 4, to define the threshold value. As shown in FIG. 8, the number of data for each segmentation result is as follows.

Examples of ID=1 (segmentation result normal): 805 cases
Examples of ID=2 (too much white matter included): 4 cases
Examples of ID=3 (too much cerebrospinal fluid included): 13 cases
Examples of ID=4 (almost no gray matter observed): 0 cases
Examples of ID=5 (deviation of overall shape and position is large): 8 cases
Examples of ID=6 (too much noise and blur): 4 cases
Examples of ID=7 (lacking large area): 0 cases Note that because the occurrence or non-occurrence of segmentation error in the example of ID=4 (almost no gray matter is observed) and the example of ID=7 (lacking large area) could easily be distinguished by visual confirmation of the Z-score map, they were not taken into consideration in the present embodiment.

In the frequency distribution figure of FIG. 6, the horizontal axis shows the ID that identifies the terms of the segmentation result, and the vertical axis shows the evaluation value calculated by step 33 in FIG. 5. The evaluation value shown in FIG. 6 is obtained by equation (6).

In FIG. 6, the plots for the example with the normal segmentation results are surrounded by a solid-line rectangle and the plots for the example with errors in the segmentation result are surrounded by a dotted-line rectangle. In FIG. 6, distinguishing is performed with threshold=0.8 and segmentation results with values equal to or above the threshold value are considered to be error, while segmentation results with values below the threshold value are considered normal.

In FIG. 6, the reason the threshold value was defined as 0.8 is described by FIG. 7. In the graph of the distinguishing performance of FIG. 7, the horizontal axis is the evaluation value (or threshold value) and the vertical axis is the sensitivity and specificity.

The sensitivity refers to the value defined as "the probability of determining what should be determined as positive (in the present embodiment, that "the segmentation result is not normal") correctly as positive." High sensitivity (being highly sensitive) refers to the state in which "the probability of determining what should be determined positive correctly as positive is high" or the state in which "the probability of mistakenly determining what should be determined positive as being negative is low."

The specificity differs from sensitivity, and is decided by the balance with the sensitivity, as shown in FIG. 7. Specificity is the value defined as "the probability of determining what should be determined as negative (in the present embodiment, that "the segmentation result is normal") correctly as negative." High specificity (being highly specific) refers to a state in which "the probability of determining what should be determined negative correctly as negative is high" or "the probability of mistakenly determining what should be determined negative as being positive is low."

In the present embodiment, the purpose is to notify the diagnostician that a segmentation error has occurred or that there is a possibility of segmentation error occurring in the tissue segmentation process, in order to eliminate the possibility of a critical misdiagnosis when the diagnostician makes a diagnosis without noticing the segmentation error. Thus, the threshold is defined so that high sensitivity is obtained. That is, the value should preferably be set value so that a state which should be determined as "abnormal segmentation result" is correctly determined as being an "abnormal segmentation result."

From the graph of FIG. 7, when the value at which the sensitivity becomes 100% and the highest specificity is obtained is defined as the threshold value, the threshold value=0.8.

In FIG. 8, the sensitivity and specificity at which the threshold value=0.8 is shown. When the threshold value=0.8, all segmentation errors in ID=2 to 7 are recognized as segmentation error, and the sensitivity=100%. Further, even for the normal example of ID=1, most are recognized as normal, and high specificity (specificity=99.5%) was obtained.

As described above, the medical image processing device 1 allows the diagnostician to be notified when segmentation error occurs, or when there is a possibility of segmentation error occurring, in the tissue segmentation process.

In particular, since the medical image processing device 1 automatically distinguishes the segmentation result of the tissue segmentation process, no burden is placed on the diagnostician.

Further, when the medical image processing device 1 determines that a segmentation result is abnormal, a warning information that a segmentation error has occurred or that there is a possibility of segmentation error occurring is outputted, along with the diagnosis support information. Thus, there is no chance for the diagnostician to make a diagnosis without noticing the segmentation error.

Further, since the medical image processing device 1 displays a segmentation result display screen showing the segmentation result only when the segmentation result is recognized as being abnormal, the diagnostician does not feel burdened.

Further, the medical image processing device 1 memorizes the voxel values or the per-voxel statistical values of the gray matter tissue for the brain image group for which the tissue segmentation process was performed normally, in the normal tissue segmentation image database 34, and further, reflects the voxel value of the gray matter image of the target test subject, which was recognized as being normal, onto the normal tissue segmentation image database 34. Thus, the accuracy of the calculation process for the evaluation value improves, leading to an improvement of the distinguishing process.

Note that even though in the above description, the normal tissue segmentation image database 35 was described as memorizing everything regardless of the attributes of the test subject or the imaging conditions, the normal tissue segmentation image database 35 may be set to memorize data according to the attributes of the test subject and the imaging condition. The attributes of the test subject are, for example, gender, age, etc. The imaging conditions are MRI model name, magnetic field intensity, voxel number, size of FOV (Field of View), slice thickness, imaging time, TR (Repetition Time), TE (Echo Time), FA (Flip Angle), etc. In this case, the medical image processing device 1 calculates the per-voxel statistical value according to the attributes of the test subject or the imaging conditions. Further, when calculating the evaluation value of step 33 in FIG. 5, the medical image processing device 1 inserts the per-voxel statistical value to the evaluation function in accordance with the attributes of the target test subject or the imaging condition of when the brain image of the target test subject was taken.

Although preferred embodiments of the medical image processing device etc. of the present invention have been described in detail above with reference to the accompanying figures, the present invention is not limited to such embodiments. It should be obvious to those in the field that examples of various changes and modifications are included within the realm of the technical idea of the present invention, and it should be understood that such examples are included in the technical scope of the present invention.

DESCRIPTION OF NOTATION

1 medical image processing device
10 user interface unit
11 image input function
12 result output function
20 processing unit
21 image processing function
22 statistic processing function
23 distinguishing processing function
30 database unit
31 white matter brain image template
32 gray matter brain image template
33 healthy subject image database
34 disease-specific ROI
35 normal tissue segmentation image database

The invention claimed is:

1. A medical image processing device, comprising:
an input means for inputting a brain image of a test subject, the brain image being made up of voxels, each of the voxels having a respective value;
a segmentation means for segmenting gray matter tissue by performing a tissue segmentation process on the brain image of the test subject and creating a resultant tissue segmented image;
a memorizing means for saving an image group of gray matter tissues of healthy subjects;
a memorizing means for saving normal tissue segmentation images;
an output means for outputting diagnosis support information based on statistical comparison between the resultant tissue segmentation image of the test subject obtained by the segmentation means and the image group of gray matter tissues of healthy subjects; and
a distinguishing means for distinguishing between normal and abnormal results or segmentation by the segmentation means, based on the voxel value of the resultant tissue segmented image for the brain image of the test subject and per-voxel statistical value of the normal tissue segmentation images, wherein
a per-voxel statistical value of the normal tissue segmentation images is represented, at every position, by an average value and a standard deviation of respective distribution of the voxel values according to a position to which each image of the normal tissue segmentation images corresponds, and then
the distinguishing means distinguishes between normal and abnormal results of segmentation by the segmentation means by comparing, against a predefined threshold value, an average value over the whole of the resultant tissue segmented images of an absolute Z-score determined from the voxel value of the resultant tissue segmented image for the brain image of the test subject, and the average value and the standard deviation at a position to which the normal tissue segmentation images corresponds.

2. The medical image processing device of claim 1, further comprising:
a memorizing means for memorizing the average value and the standard deviation at every voxel to which each image corresponds substituting for the memorizing means for memorizing the normal tissue segmentation images, and
a reflection means for reflecting the voxel value of the gray matter tissue for the brain image of the test subject, which is distinguished as normal by the distinguishing means, to the memorizing means.

3. The medical image processing device of claim 1, further comprising:
a warning means for outputting a warning information when the distinguishing means recognizes the result of the segmentation as an abnormal result.

4. The medical image processing device of claim 1, further comprising:
a display means for displaying the segmentation result by the segmentation means when the distinguishing means recognizes the result of the segmentation as an abnormal result.

5. A medical image processing method, comprising:
an input step of inputting brain image of a test subject;
a segmentation step of segmenting gray matter tissue by performing a tissue segmentation process on the brain image of the test subject;
an output step of outputting diagnosis support information based on statistical comparison between the gray matter tissue image of the test subject obtained by the segmentation step and the image group of gray matter tissues of healthy subjects; and
a distinguishing step of distinguishing between normal and abnormal result of segmentation in the segmentation step, based on the voxel value of the gray matter tissue for the brain image of the test subject and the per-voxel statistical value of the gray matter tissue for the brain image group, for which the tissue segmentation process has been performed normally, wherein
the distinguishing step distinguishes between normal and abnormal result of segmentation by the segmentation means by comparing the absolute Z-score of the voxel value of the gray matter tissue for the brain image of the test subject against a predefined threshold value.

6. A non-transitory computer-readable medium containing a program for causing a processing device to perform:
inputting a brain image of a test subject, the brain image being made up of voxels, each of the voxels having a respective value;
segmenting gray matter tissue by performing a tissue segmentation process on the brain image of the test subject and creating a resultant tissue segmented image;
saving an image group of gray matter tissues of healthy subjects;
saving normal tissue segmentation images;
outputting diagnosis support information based on statistical comparison between the resultant tissue segmentation image of the test subject obtained by the segmentation means and the image group of gray matter tissues of healthy subjects; and
distinguishing between normal and abnormal results of segmentation by the segmentation means, based on the voxel value of the resultant tissue segmented image for the brain image of the test subject and the per-voxel statistical value of the normal tissue segmentation images, wherein a per-voxel statistical value of the normal tissue segmentation images is represented, at every position, by an average value and a standard deviation of respective distribution of the voxel values according to a position to which each image of the normal tissue segmentation images corresponds, and then distinguishing between normal and abnormal results of segmentation by comparing, against a predefined threshold value, an average value over the whole of the resultant tissue segmented images of an absolute Z-score determined from the voxel value of the resultant tissue segmented image for the brain image of the test subject, and the average value and the standard deviation at a position to which the normal tissue segmentation images corresponds.

7. The medical image processing device of claim 2, further comprising:

a warning means for outputting a warning information when the distinguishing means recognizes the result of the segmentation as an abnormal result.

8. The medical image processing device of claim 2, further comprising:

a display means for displaying the segmentation result by the segmentation means when the distinguishing means recognizes the result of the segmentation as an abnormal result.

9. The medical image processing device of claim 3, further comprising:

a display means for displaying the segmentation result by the segmentation means when the distinguishing means recognizes the result of the segmentation as an abnormal result.

10. The medical image processing device of claim 7, further comprising:

a display means for displaying the segmentation result by the segmentation means when the distinguishing means recognizes the result of the segmentation as an abnormal result.

* * * * *